US006264952B1

(12) United States Patent
Enright et al.

(10) Patent No.: US 6,264,952 B1
(45) Date of Patent: Jul. 24, 2001

(54) METHOD FOR PROTECTING A MAMMALIAN HOST AGAINST INFECTION BY BRUCELLA

(75) Inventors: Frederick M. Enright, Baton Rouge, LA (US); Alexander J. Winter, Ithaca, NY (US); Gerhardt G. Schurig, Blacksburg, VA (US); John H. Wyckoff, III, Stillwater, OK (US)

(73) Assignees: Board of Supervisors of Louisiana State University and Agricultural and Mechanical College, Baton Rouge, LA (US); Virginia Polytechnic Institute and State University, Blacksburg, VA (US); Board of Regents for Oklahoma State University, Stillwater, OK (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 08/989,089

(22) Filed: Dec. 11, 1997

Related U.S. Application Data

(63) Continuation of application No. 08/705,044, filed on Aug. 29, 1996, now abandoned, which is a continuation of application No. 08/148,158, filed on Nov. 5, 1993, now abandoned.

(51) Int. Cl.[7] .......................... A61K 39/00; A61K 39/02; A01N 63/00; C12N 1/00

(52) U.S. Cl. .................................... 424/184.1; 424/234.1; 424/93.1; 424/93.4; 424/823; 424/824; 435/243; 435/822

(58) Field of Search ............................. 424/184.1, 234.1, 424/93.1, 93.4, 823, 824; 435/243, 822

(56) References Cited

U.S. PATENT DOCUMENTS

| | | | |
|---|---|---|---|
| 3,449,209 | 6/1969 | Cameron | 195/96 |
| 3,515,708 | 6/1970 | Williams | 424/92 |
| 4,340,588 | 7/1982 | Woodard | 424/92 |
| 4,687,666 | 8/1987 | O'Daly | 424/88 |
| 4,764,370 | 8/1988 | Fields et al. | 424/93 |
| 4,959,211 | 9/1990 | Lombardo et al. | 424/93 |
| 4,963,354 | 10/1990 | Shepard et al. | 424/85.1 |
| 5,190,860 | 3/1993 | Adams et al. | 435/7.32 |

FOREIGN PATENT DOCUMENTS 230775 12/1985 (DE) .

OTHER PUBLICATIONS

Adams, L.G., "Development of Live Brucella Vaccines" in L.G. Adams (Ed.), Advances in Brucellosis Research, pp. 250–267 (1990).

Brett, S.J. et al., "Interactions of *Mycobacterium lepraemurium* with Resident Peritoneal Macrophages; Phagocytosis and Stimulation of the Oxidative Burst," Clin. Exp. Immunol., vol. 71, pp. 32–38 (1988).

Chai et al., "A 'Live' Vaccine of Non–replicatable *pasteurella multocida* FS3 Cells Prepared by Psoralen Treatment and Long Wave UV Radiation," Israel Journal of Vet. Med., vol. 44, pp. 195–201 (1988).

de Bagues, M. et al., "Vaccination with Live *Brucella abortus* RB51 Provides Protection in Mice against *B. abortus, B. melitensis*and *B. ovis*," Abstracts of Papers Presented at the 73rd Annual Meeting of the Conference of Research Workers in Animal Diseases, p. 17 (Nov. 9–10, 1992).

de Bagues, M. et al., "Vaccination with *Brucella abortus* Rough Mutant RB51 Protects BALB/c Mice against Virulent Strains of *Brucella abortus, Brucella melitensis*, and *B. ovis*," Infection and Immunity, vol. 62, pp. 4990–4996 (1994).

Dima et al., "Oral Immunizatin of the Newly Born Guinea Pig With Dysenteric Vaccine Irradiated With Gamma Radiationsssss ($^{60}$Co)," Revue Roumaine de Biochemie, vol. 22, pp. 183–189 (1985).

Dranovskaia et al., Rudiobiologia, vol. 26, pp. 74–78 (1986) (Abstract).

Dzata, G. et al., "The Effects of Adjuvants on Immune Responses in Cattle Injected with a *Brucella abortus* Soluble Antigen," Veterinary Microbiology, vol. 29, pp. 27–48 (1991).

(List continued on next page.)

*Primary Examiner*—Lynette R. F. Smith
*Assistant Examiner*—Li Lee
(74) *Attorney, Agent, or Firm*—John H. Runnels

(57) ABSTRACT

Vaccines against facultative intracellular pathogens are disclosed. A host is vaccinated with non-viable but metabolically active agents. The non-viable agents produce immunogenic components that elicit protective host immune responses, with minimal likelihood of host infection by the vaccine agent. Living agents, either attenuated or virulent, are exposed to a dose of gamma irradiation (or other strong mutagen) that is sufficient to limit or prevent the replication of the agents within the host, but that is insufficient to stop the metabolic activities of the agent. In vitro exposure of a microbial agent to the damaging effects of gamma irradiation or of another strong mutagen induces certain stress responses in the infectious agent. These stress responses are similar to the stress responses that the virulent agent would produce within the tissues of the host. The stress responses include the production of antigens that stimulate appropriate host immune responses when the irradiated agent is used in a vaccine. Examples of facultative intracellular pathogens for which non-viable vaccine agents may be made in accordance with the present invention include various bacterial pathogens (e.g., Brucella sp., *Brucella abortus*, Mycobacterium sp., *Mycobacteriun lepraemurum, Mycobacterium tuberculosis*, Salmonella sp., *Salmonella typhimurium*); various mycotic pathogens (e.g., Blastomyces, Histoplasma, Cocidioides); and various protozoal pathogens (e.g., Leishmania, Trypanosomas).

6 Claims, No Drawings

OTHER PUBLICATIONS

Dzata, G. et al., "Immunopotentiation of Cattle Vaccinated with a Soluble *Brucella abortus* Antigen with Low LPS Content: An Analysis of Cellular and Humoral Immune Responses," Veterinary Microbiology, vol. 29, pp. 15–26 (1991).

Eisenberg et al., "Gamma–Irradiated Scrub Typhus Immunogens: Development and Duration of Immunity," Infect. & Immun., vol. 22, pp. 80–86 (1978).

Finlay, B.B. et al. "Salmonella: A Model to Study Intracellular Parasitism" in L.G. Adams (Ed.), Advances in Brucellosis Research, pp. 111–118 (1990).

Finlay, C.A. et al., "Activating Mutations for Transformation by p. 53 Produce a Gene Product That Forms an hsc70–p53 Complex with an Altered Half Life," Mol. Cell. Biol., pp. 531–539 (1988).

Howard, J.G., et al., "Prophylactic Immunization against Experimental Leishmaniasis," J. Immunology, vol. 129, pp. 2206–2212 (1982).

Hoyer et al., "Polynucleotide Homologies of Brucella Deoxyribunucleic Acids," Journal of Bacteriology, vol. 95, pp. 444–448 (1968).

Kaufman, S.H.E., "Heat Shock Proteins and the Immune Response," Immunology Today, vol. 11, pp. 129–136 (1990).

Kuby, J., "Designing Vaccines for Active Immunization," pp. 473–474 in J. Kuby, Immunology (2nd ed. 1994).

Levinson et al., Production of Potent Inactivated Vaccines with Ultraviolet Irradiation, J.A.M.A., vol. 125, pp. 531–532 (1944).

Neidhardt, F.C. et al., The Genetics and Regulation of Heat Shock Proteins, Ann. Rev. Genet., vol. 18, pp. 295–329 (1984).

Nicoletti, P., "Vaccination," Chapter 11 in K. Nielsen et al., Animal Brucellosis, pp. 283–299 (1990).

Plommet, M. "Killed Vaccines in Cattle: Current Situations and Prospects" in L.G. Adams (Ed.), Advances in Brucellosis Research, pp. 215–227 (1990).

Schlingman et al., "Inactivated *Brucella abortus* as an immunizing agent in catle," Proceedings of Fifty–Third Annual Meeting of the United States Livestock Sanitary Association, pp. 48–57 (1949).

Schlingman et al., "Further Observations in Inacativated *Brucella abortus* as an immunizing agent in catleee," The North American Veterinarian, vol. 33, pp. 397–405 (1952).

Sonnenwirth et al., Microbiology, 3rd Ed., Chapter 33, pp. 686–691 (1985).

Srivastava, P.K. et al., "Tumor Rejection Antigens of Chemically Induced Sarcomas of Inbred Mice," Proc. Natl. Acad. Sci. USA, vol. 83, pp. 3407–3411 (1986).

Ullrich, S.J. et al., "A Mouse Tumor–Specific Transplantation Antigen is a Heat Shock–Related Protein," Proc. Natl. Acad. Sci. USA, vol. 83, pp. 3121–3125 (1986).

Vandenberg, "Protective Immunity Produced by the Injection of X–Irradiated sporozoites of *Plasmodium Berghei*," The Journal of Parasitology, vol. 54, pp. 1175–1180 (1968).

Verger et al., "Brucella, a monospecific genus as shown by Deoxyribonucleic Acid Hybridization," International Journal of Systematic Bacteriology, vol. 35, pp. 292–295 (1985).

Wyckoff, J.H. et al., "Comparison of *Brucella abortus* Antigen Preparations for in vitro Stimulation of Immune Bovine T–Lymphocyte Cell Lines," Vet. Immunol. Immunopathol., vol. 36, pp. 45–64 (1993).

Young, D. et al., "Stress–Induced Proteins as Antigens in Infectious Diseases" in M.L. Pardue et al. (Eds.), Stress–Induced Proteins, pp. 275–285 (1989).

Young, R. A., "Stress Proteins and Immunology," Ann. Rev. Immunology, vol. 8, pp. 401–420 (1990).

Plommet, M. et al., "Vaccines, Vaccination in Brucellosis," Ann. Inst. Pasteur (Microbiol.), vol. 138, pp. 117–121 (1987).

Olsen et al. "Lymphocyte Proliferative Responses of Goats Vaccinated With *Brucella Melitensis* 16M or a ΔpurE210 Strain" Infection and Immunity 65 (7)=2987–2991, Jul. 1997.*

Carcia–Carrillo Zb1 Vet Med 13, 28 =425–431, 1981.*

* cited by examiner

METHOD FOR PROTECTING A MAMMALIAN HOST AGAINST INFECTION BY BRUCELLA

This application is a continuation of application serial number 08/705,044, filed Aug. 29, 1996, now abandoned; which is a continuation of application Ser. No. 08/148,158, filed Nov. 5, 1993, now abandoned.

This invention pertains to a method for protecting a mammalian host against infection by Brucella.

A host generally receives the greatest degree of immunity from actual infection by a pathogenic agent. The resulting immunity is specific, long-lasting, and complete—but of course is useful only if the host survives the disease produced by the pathogen. The goal of all vaccinations is to induce the same degree of solid immunity, but without any associated risk of disease; in reality few vaccines meet this ideal standard. Vaccines are often based either on live attenuated pathogenic agents, or on killed agents. The degree of protection provided by both types of vaccines is highly variable.

A facultative intracellular pathogen is a pathogen that is adapted to survive in a host by living within the host's cells, but that can also survive outside host cells at least for a time, depending on the environment it faces. As a general observation, immunity to facultative intracellular pathogens in a vaccinated host is better achieved with a vaccine made from living attenuated agents than with a vaccine made from killed agents. Immunity results from the survival of the living agents within the targeted host tissues for time sufficient to stimulate an appropriate host immune response. See Davis et al., *Microbiology*, p. 472 (1967); and P. Nicoletti, "Vaccination," Chapter 11 in K. Nielsen et al., *Animal Brucellosis*, pp. 283–299 (1990). An appropriate immune response to intracellular pathogens generally depends on the activity of T-lymphocytes. Vaccines made from killed agents frequently produce only humoral immune responses (i.e., antibodies), which are generally less effective in protecting the host against subsequent infection by the virulent intracellular pathogen.

The main risk associated with attenuated live vaccines is that an attenuated vaccine strain can occasionally infect the host and produce disease. Vaccine-induced infection and disease can result from at least three different causes: (1) The vaccine agent may be insufficiently attenuated. (2) The host immune system may be so compromised that it cannot eliminate the attenuated agent. (3) The attenuated agent may spontaneously revert back to a virulent phenotype. For example, it was recently discovered that the genome of the attenuated polio-1 virus used in the Sabin polio vaccine is identical to the wild-type virulent strain in all but two base pairs; thus reversion of this attenuated virus to the wild-type will occur at a statistically predictable frequency.

Even though the medical community recognizes the value of the immunity produced by a variety of living attenuated vaccines, the risk of infection in the vaccinated host has limited their use.

Different intracellular pathogens may gain entrance into host cells by different mechanisms; they may prefer different host cell types; and they may prefer to localize in different cellular compartments. Advantages of an intracellular habitat (for the pathogen) include a degree of protection from the antimicrobial systems of the host, including protection from the host's antibodies, complement, phagocytic white blood cells, and cytotoxic non-phagocytic white blood cells. This shielding from components of the host immune system interferes with the host's ability to mount a specific protective immune response against the agent.

Disadvantages of an intracellular habitat (for the pathogen) include exposure to a wide variety of potential stresses created by the cell, such as altered pH, suboptimal nutrient levels, above-optimal temperatures, membrane damaging enzymes and peptides, and reactive free radicals that can attack both membranes and DNA.

The balance between the advantages of intracellular life and its disadvantages determines not only how long an intracellular pathogen will survive, but also its ability to synthesize virulence factors (factors giving the agent an additional advantage and causing disease in the host), as well as the severity of the resulting disease.

Despite the lack of a general understanding of how a host develops immunity to intracellular pathogens, several typical characteristics of efficacious vaccines to these agents have been identified. The most effective immunity to such agents usually results from infection of the host by the virulent agent itself, resulting in clinical or nonclinical infection, and full stimulation of an appropriate immune response. The most effective immunity to such agents is usually cell-mediated, rather than humoral. Selected subclasses of T-lymphocytes that recognize unique antigenic determinants in the agent, or that recognize determinants associated with the agent, are clonally expanded. Such lymphocytes are then able to activate phagocytic white blood cells to kill the intracellular agents. In some instances the lymphocytes themselves recognize unique antigens associated either with the agent or with a host cell infected with the agent, and synthesize and secrete antimicrobial compounds such as perforins.

Antibodies do not appear to play a large role in protecting the host from intracellular pathogens, or in clearing infections caused by intracellular pathogens. In fact, the antigenic structures recognized by antibody-secreting lymphocytes may have little in common with the antigenic structures responsible for effective cell-mediated immune protection.

Intracellular agents that have been grown on artificial growth media (where possible), collected, washed, and killed (e.g., by heat or chemical denaturation), and then administered to a susceptible host, rarely provide immune protection against the virulent living agent when the host is naturally or experimentally challenged. Agents prepared in this manner do result in the production of specific antibodies by the "vaccinated" host; however, these antibodies do not necessarily confer protection from infection, because the pathogens inhabit intracellular sites not typically reached by antibodies.

It has been previously demonstrated that exposure of a susceptible host to a living, less virulent form of the agent can result in long-lived immunity. The resulting immunity tends to be cell-mediated, as is the immunity resulting from natural infection. The attenuated (nonvirulent) agent must generally spend some time within the host before immunity develops, colonizing the same cells and tissues of the host as does the virulent agent. By contrast, immunity will generally be incomplete or absent if the chosen attenuated agent fails to survive within host tissues for a long enough period of time for a complete immune response to develop, or if the attenuated agent parasitizes a different cell type than does the virulent agent.

M. de Bagues et al., "Vaccination with Live *Brucella abortus* RB51 Provides Protection in Mice against Virulent *B. abortus, B. melitensis*, and *B. ovis*," Abstracts of Papers Presented at the 73 rd Annual Meeting of the Conference of Research Workers in Animal Diseases, p. 17 (Nov. 9–10, 1992) (which is not prior art to the present application), discloses certain Brucella vaccinations, including Brucella vaccinations with gamma-irradiated cells.

U.S. Pat. No. 3,449,209 discloses an attenuated live Brucella vaccine. U.S. Pat. No. 4,764,370 discloses an attenuated live Salmonella vaccine.

U.S. Pat. Nos. 3,515,708 and 4,340,588 disclose killed Brucella vaccines. U.S. Pat. No. 4,687,666 discloses a killed Leishmania vaccine.

U.S. Pat. No. 4,959,211 discloses viral vaccines prepared by irradiating the virus.

U.S. Pat. No. 4,963,354 discloses a vaccine against a fibrosarcoma in which the fibrosarcoma cells used in the vaccine were gamma-irradiated at a radiation level that ultimately killed the cells, but that left the cells metabolically viable for a time prior to the cells' death.

U.S. Pat. No. 5,190,860 discloses mice immunized with an irradiated *B. abortus* strain for the purpose of raising monoclonal anti-Brucella antibodies. J. G. Howard et al., "Prophylactic Immunization against Experimental Leishmaniasis," J. Immunology, vol. 129, pp. 2206–2212 (1982) reported immunizing mice with gamma-irradiated live Leishmania promastigotes. However, the authors reported that "irradiated promastigotes do not commend themselves as the basis of a vaccine." (At page 2211.) U.S. Pat. No. 4,687,666, cited above, reported that the Howard et al. irradiated promastigote vaccine did not give satisfactory results. (Col. 1, lines 31–45.)

As one example of the need for improved vaccines against facultative intracellular pathogens, Brucellosis is a disease affecting livestock and humans throughout the world. The disease is caused by five species of the bacterial genus Brucella. Humans are typically infected through contact with infected livestock, or by consumption of Brucella sp-contaminated food or dairy products. Several live attenuated vaccines have been used to control, although not eliminate, Brucella sp infections in animals. Years of research have failed to find an effective Brucella whole killed vaccine, killed extracted vaccine, or subunit or component vaccine. M. Plommet, "Killed Vaccines in Cattle: Current Situations and Prospects" in L. G. Adams (Ed.), *Advances in Brucellosis Research*, pp. 215–227 (1990). Live attenuated vaccines, by contrast, are usually effective in animals, but can occasionally result in infections in vaccinated animals, can result in abortions, and may induce prolonged serological responses interfering with diagnosis. The live attenuated vaccines are virulent to humans, and therefore cannot be used in humans. L. G. Adams, "Development of Live Brucella Vaccines" in L. G. Adams (Ed.), *Advances in Brucellosis Research*, pp. 250–276 (1990); S. J. Revich et al., "Human Infection by *Brucella abortus* Strain 19," Can. J. Public Health, vol. 52, pp. 285 *ff* (1961). There is no safe and effective vaccine for Brucellosis in humans. J. Kolar, "Brucellosis in Eastern European Countries" in E. J. Young et al. (Eds.), *Brucellosis: Clinical and Laboratory Aspects*, pp. 163–172 (1989).

A common feature of both of the commonly used live attenuated Brucella vaccine strains (*Brucella abortus* strain 19 and Rev 1 *Brucella melitensis*) is that they localize and survive within the lymphoid tissues of the host for a time, much as do their virulent counterparts. Survival of the vaccine strains for at least two weeks in these organs is not unusual. The vaccine strains stay alive and replicate within the cells of the reticuloendothelial system of the lymphoid organs. These vaccine strains are usually (but not always) eliminated from these tissues by the combined action of phagocytic leukocytes, immune T-lymphocytes, and perhaps antibodies. The specific antigenic determinants from the live attenuated vaccine strains triggering the protective immune responses are not known. It is likely that these antigenic determinants are protective in nature for the Brucella, and are not sufficiently expressed until the vaccine organisms have interacted with the host. Neither heat-killed nor chemically-killed Strain 19 or Rev 1 strain produces a vaccine effective in protecting animals against infection.

A novel approach to vaccination against facultative intracellular pathogens has been discovered. In the novel method, the host is vaccinated with non-viable but metabolically active agents. The non-viable agents produce immunogenic components that elicit protective host immune responses, with minimal likelihood of host infection by the vaccine agent.

Living agents, either attenuated or virulent, are exposed to a dose of gamma irradiation (or other strong mutagen) that is sufficient to limit or prevent the replication of the agents within the host, but that is insufficient to stop the metabolic activities of the agent. The agents remain metabolically active, and are thus able to produce immunogenic compounds capable of stimulating the hosts' protective immune responses, or to maintain the production of such immunogenic compounds.

In vitro exposure of a microbial agent to the damaging effects of gamma irradiation or of another strong mutagen, e.g. a radiomimetic chemical, induces certain stress responses in the infectious agent. These stress responses are similar to the stress responses that the virulent agent would produce within the tissues of the host. The stress responses include the production of antigens that stimulate appropriate host immune responses when the irradiated agent is used in a vaccine. Such vaccination results in host immunity to infection by the counterpart virulent agent.

The host-agent interactions that cause effective immunity against an intracellular pathogen are largely unknown. We hypothesize (without wishing to be bound by this theory) that the agent is exposed to a variety of stresses characterizing an intracellular existence; in response to these stresses, the agent synthesizes a number of antigens, such as proteins or other molecules that are otherwise unexpressed, or that are constitutively expressed in lower concentrations under non-adverse conditions. These antigens were originally described as "heat shock" proteins; however, it is now known that stresses other than heat will induce the expression of many of these proteins. Thus they are now generally called "stress response" proteins. Many of these proteins have been described, and their functions in protection of the stressed agent and in immune responses have been documented. See R. A. Young, "Stress Proteins and Immunology," Ann. Rev. Immunology, vol. 8, pp. 401–420 (1990).

The role of stress response proteins in activating the host's immune system is less well characterized. It is hypothesized that the expression of one or more proteins induced by a stress response of the agent, or alternatively the expression of one or more proteins by an infected host cell, may stimulate a protective immune response.

Increased levels of stress response proteins have been observed in virus-transformed cells, as well as in chemically-induced tumor cells. C. A. Finlay et al., "Activating Mutations for Transformation by p53 Produce a Gene Product That Forms an hsc70-p53 Complex with an Altered Half Life," Mol. Cell. Biol., pp. 531–539 (1988). Stress response proteins have been implicated in the recognition and rejection of transformed cells. See P. K. Srivastava et al., "Tumor Rejection Antigens of Chemically Induced Sarcomas of Inbred Mice," Proc. Natl. Acad. Sci. USA, vol. 83, pp. 3407–3411 (1986); and S. J. Ullrich et al., "A Mouse Tumor-Specific Transplantation Antigen is a Heat Shock- Related Protein," Proc. Natl. Acad. Sci. USA, vol. 83, pp. 3121–3125 (1986).

The stress response proteins of both eukaryotic and prokaryotic cells are highly conserved between species. Their synthesis may be induced by a number of host effector mechanisms, including elevated temperatures, formation of toxic free radicals, and deprivation of nutrients. The organisms may also be induced to form stress response proteins by exposure to gamma radiation or other strong mutagens. Many of the radiation- or mutagen-induced stress response proteins are the same as the host-induced stress response proteins.

Mycobacterial stress proteins are immunodominant targets for both murine antibody and T-lymphocyte immune responses. Approximately 20% of mycobacterial-reactive $CD4^+$ T-lymphocytes in mice previously immunized with *Mycobacterium tuberculosis* recognize the hsp60 stress protein of that agent. See R. A. Young, "Stress Proteins and Immunology," Ann. Rev. Immunology, vol. 8, pp. 401–420 (1990); and S. H. E. Kaufmann, "Heat Shock Proteins and the Immune Response," Immunology Today, Vol. 11, pp. 129–136 (1990). It is possible that immune responses to these stress proteins may provide a general level of protection against the earlier events in the infectious process. This initial protection would then be reinforced by secondary immune responses to specific unique antigenic determinants of the agent. Up-regulation during infection may be an important factor in the generally better immunity provided by live organisms. See D. Young et al., "Stress-Induced Proteins as Antigens in Infectious Diseases" in M. L. Pardue et al. (Eds.), *Stress-Induced Proteins*, pp. 275–85 (1989).

Free radical formation by host cells is one potential source of stress to the agent. Hydroxyl radical formation is known to occur as a result of intracellular infection of host phagocytic cells. Hydroxyl radicals may damage both the host's DNA and the agent's DNA, thereby inducing the production of stress response proteins. Radiomimetic agents such as bleomycins are known. to result in DNA alteration and the expression of stress response proteins by the formation of hydroxyl radicals.

We hypothesize (without wishing to be bound by this theory) that the exposure of intracellular pathogens to gamma irradiation (or other strong mutagens) produces free radicals that alter the agent's DNA. The altered DNA invokes the protective stress response, accompanied by the production of stress response proteins. The stress-related proteins induced by irradiation are thought to simulate the stress response proteins produced by the agent when it is exposed to host-origin antimicrobial compounds. The stress response proteins, regardless of how generated, can then stimulate a protective immune response in a vaccinated host.

Alternatively, we hypothesize (without wishing to be bound by this theory) that the exposure of intracellular pathogens to gamma irradiation (or other strong mutagens) causes expression of at least one pathogen stress protein or other pathogen-synthesized molecule at a level of expression substantially greater than the level of constitutive expression by the pathogen under non-adverse conditions, and that this pathogen stress protein or other pathogen-synthesized molecule is one that can, in turn, cause a host cell to express a host stress protein or other host-cell-synthesized molecule signalling to the host's immune system that the cell is infected by a pathogen. Then this host-cell-synthesized molecule stimulates a protective immune response.

For this reason an irradiated non-viable agent can induce protective immunity whose effectiveness exceeds that produced by conventionally killed agents, and rivals the immunity produced by vaccinations with an attenuated living agent. A non-viable vaccine has an added advantage over a living vaccine in that it cannot cause a vaccine strain infection that might result in disease.

Definition. As used in this specification and in the claims below, a "non-viable" agent refers to an organism that is still capable of conducting metabolic activities, but that is unable to propagate indefinitely in an appropriate environment (either in vitro or in vivo). Examples. A boiled suspension of Brucella cells will not respire, and is therefore not considered to be a "non-viable" agent within this definition; rather, it would be considered a killed agent. On the other hand, a suspension of cells treated with a high exposure to gamma irradiation may retain the ability to conduct metabolic activities, and thus could be considered a "non-viable" agent within this definition, depending on the radiation dose used for the particular organism. Depending on the sensitivity of the particular organism to the effects of gamma irradiation, the cells may undergo several divisions before proliferation ceases; such an irradiated organism would still be considered a "non-viable" agent within this definition, because it would be unable to propagate indefinitely. Examples are given below of irradiated, non-viable Brucella and other non-viable agents.

Ionizing radiation inactivates bacteria, protozoa, fungi, and other pathogens by altering their DNA beyond the restorative capacity of the organisms' repair mechanisms. By contrast, ribosomal assemblies and RNA are more resistant to ionizing radiation, and may continue to function even when the DNA has been damaged beyond repair. B. A. Bridges, "Bacterial Reaction to Radiation," in J. G. Cook (Ed.), *Patterns of Progress, Microbiology Series*, pp. 72 *ff* (1976). Thus exposure of the agents to an appropriate dose of gamma radiation (or other mutagen) will prevent their propagation, without preventing their synthesis of some or all of the following: stress related proteins, invasion proteins, and inhibitors of phagocytosis. See generally F. C. Neidhardt et al., "The Genetics and Regulation of Heat Shock Proteins," *Ann. Rev. Genet.*, vol. 18, pp. 295–329 (1984); B. B. Finlay et al., "Salmonella: A Model to Study Intracellular Parasitism" in L. G. Adams (Ed.), *Advances in Brucellosis Research*, pp. 111–118 (1990); and S. J. Brett et al. , "Interactions of *Mycobacterium lepraemurium* with Resident Peritoneal Macrophages; Phagocytosis and Stimulation of the Oxidative Burst," C.lin. Exp. Immunol., vol. 71, pp. 32–38 (1988). Thus when such an irradiated agent is used as a vaccine, the host immune system can develop an immune response to some or all of these potential immunogens. By contrast, heat-killed bacteria do not produce as many of these proteins, and those that are produced may not be expressed in the same quantities.

Appropriate doses of gamma irradiation or other strong mutagens may be used to prevent the further replication of the facultative intracellular agents, while still allowing these organisms to synthesize biologically active molecules that aid their survival within host cells, and that stimulate the host's protective immune response. Examples of facultative intracellular pathogens for which non-viable vaccine agents may be made in accordance with the present invention include various bacterial pathogens (e.g., Brucella sp., *Brucella abortus, Brucella melitensis*, Mycobacterium sp., *Mycobacterium lepraemurum, Mycobacterium tuberculosis*, Salmonella sp., *Salmonella typhimurium*, Listeria, *Shigella flexneri, Rickettsia tsutsugamushi, Rickettsia prowazekii, Rickettsia rickettsii, Chlamydia psittaci, Chlamydia trachomatis, Chlamydia pneumoniae, Coxiella burnettii*, Yersinia sp., *Yersinia pestis, Legionella pneumonophia*, Francisella); various mycotic pathogens (e.g., Blastomyces sp., *Blastomyces dermatitides*, Histoplasma sp., *Histoplasma capsulatum*, Coccidioides, *Cryptococcus neoformans*); and various protozoal pathogens (e.g., *Leishmania donovani, Leishmania mexicani*, Trypanosoma sp., *Trypanosoma cruzi*, Toxoplasma sp., *Toxoplasma gondi*, Plasmodium, Babesia, Theileria, Isospora, and Eimeria).

Determining an appropriate dose of radiation or other mutagen to use with a particular organism will be within the ability of one of ordinary skill in the art who is given the teachings of the present specification. The dose used will be one that is high enough to prevent the further replication of the organism, while still allowing the organism to metabolize. Such a dose can readily be identified by attempting to grow the organism in a suitable medium after irradiation or other mutagenic treatment.

Strong mutagens other than radiation can be used in the practice of this invention; in particular, radiomimetic agents such as bleomycins, etoposide, and teniposide can also mimic the stress that the intracellular environment places on intracellular pathogens, and can cause the production of many of the same protective antigens by the organisms. (Bleomycins, for example, are cytotoxic glycopeptide antibiotics isolated from strains of *Streptomyces verticillus*. One bleomycin is sold under the trademark Blenoxane® by Bristol Laboratories, Syracuse, N.Y.)

Because relatively few organisms naturally survive within the host's cells to produce the protective antigens—generally as few as 100 to 1000 bacteria per gram of lymphoid tissue—irradiation of stock cultures in excess of $10^{11}$ to $10^{13}$ CFU's (colony-forming units) will produce considerably larger amounts of the desired immunogens. Furthermore, some organisms evade host defense systems by changing the antigens presented on their cell surface. For this reason, and because it is not generally known how many varieties of protective antigens are produced by a particular pathogen, the probability of the production of all potential immunogens is much greater when large numbers of organisms are simultaneously exposed to the stress of gamma radiation or other strong mutagen. Thus it is believed that immunity to a broad spectrum of possible immunogens is induced by vaccines in accordance with the present invention. This is a distinct advantage of the present invention, as it reduces a pathogen's ability to evade host immune systems by repeatedly altering surface antigens, a defense mechanism employed by some pathogens.

EXAMPLES

Example 1

Gamma-irradiated *Brucella abortus* preparations were observed to be superior to preparations of heat-killed *B. abortus* in stimulating the in vitro proliferation of immune bovine T-lymphocyte cell lines. The irradiated bacteria synthesized at least eight proteins that were not produced by the heat-killed *B. abortus*. The irradiated organism also synthesized greater quantities of at least five protein bands that were shared with the heat-killed bacteria. Thus the gamma-irradiated *B. abortus* provided in vitro antigenic stimuli that were deficient in the heat-killed cells. For additional details, see J.H. Wyckoff et al., "Comparison of *Brucella abortus* Antigen Preparations for in vitro Stimulation of Immune Bovine T-Lymphocyte Cell Lines," Vet. Immunol. Immunopathol., vol. 36, pp. 45–64 (1993) (not prior art to this application), the entire disclosure of which is incorporated by reference.

Example 2

*Brucella abortus* strain RB51 was cultured on tryptose agar at 37° C. in 7.0% $CO_2$ for 72 hours. The bacterial lawn was scraped from the solid agar and suspended in 30 ml of tryptose broth to give a concentration of at least $1.0\times10^{10}$ viable bacteria per ml. This suspension of bacteria, placed in a 100 ml screw cap bottle, was immediately subjected to Cobalt-60 irradiation at 2.2 Krads/min for 495 minutes, for a total irradiation of 1.089 Mrads. One hundred $\mu$l of the irradiated bacterial suspension was directly plated onto tryptose agar and cultured for one week at 37° C. in 7% $CO_2$ to verify that the bacteria were unable to replicate, and were therefore "non viable." (This step ran for a time sufficient to have identified even a single bacterium capable of unrestrained replication, had there been such a bacterium in the original irradiated suspension.) The remainder of the suspension of irradiated bacteria was divided into 26, 1 ml freezer vials, which were flash frozen in liquid nitrogen. The frozen bacterial suspensions were stored at −70° C. until used. Selected vials were determined to contain approximately $2.0\times10^{11}$ bacteria per vial (based on dry weight). After thawing, irradiated bacterial suspensions were centrifuged and washed in physiological saline. Washed bacteria were resuspended in physiological saline and used in the immunizations described below.

Examples 3–7

Female BALB/c mice approximately 10 weeks of age were randomly divided into 5 treatment groups of 5 mice each. Group 1 mice were inoculated intraperitoneally with live *B. abortus* strain RB51 at a dose of $3.0\times10^{8}$ CFU, with no adjuvant. Group 2 mice were inoculated intraperitoneally with 20 $\mu$g dry weight (approximately $1.0\times10^{9}$ CFU) methanol-killed *B. abortus* strain RB51, mixed with a commercial adjuvant (QS-21) (Cambridge BioScience, Cambridge, Mass.). Group 3 mice were inoculated intraperitoneally with the equivalent of 20 $\mu$g dry weight of the gamma-irradiated *B. abortus* strain RB51 (approximately $1.0\times10^{9}$ CFU), with the QS-21 Adjuvant. Group 4 mice were inoculated subcutaneously with $5.0\times10^{4}$ CFU of living *B. abortus* strain 19 with no adjuvant. Group 5 (the control) received an intraperitoneal inoculation of phosphate-buffered saline.

All groups were given inoculations on Day 0 of the study. On Day 28, groups 2 and 3 were reinoculated as described above. On Day 35, all five groups were inoculated intravenously with $5.0\times10^{4}$ CFU of living *B. abortus* strain 2308 (the virulent *B. abortus* challenge strain). On Day 42, all mice were killed, and their spleens were removed and cultured to determine the number of virulent *B. abortus* challenge strain organisms colonizing the organ.

Mice in Group 5 (the control group) had a mean log 6.6 *B. abortus* per spleen (i.e., $10^{6.6}$ bacteria per spleen). Group 1 mice (those receiving live RB51) had a mean log 0.91 reduction of challenge strain *B. abortus* versus the control group. Group 2 mice (those receiving the killed RB51 with adjuvant) had a mean log 0.1 reduction in challenge bacteria per spleen. Group 3 mice (those receiving the gamma-irradiated *B. abortus* and adjuvant) had a mean log 0.43 reduction in challenge bacteria per spleen. The group 4 mice (those receiving live strain 19 *B. abortus*) had a mean log 2.12 reduction in the number of challenge bacteria per spleen.

The reduction of colonization of the spleen with the challenge bacteria was significant at $P\leqq0.001$ for group 1, at $P\leqq0.05$ for group 3, and at $P\leqq0.001$ for group 4. There was no significant reduction in colonization of spleen with the challenge strain of bacteria in group 2 as compared to control group 5. The adjuvant QS-21 alone conferred no protection to challenged mice (data not shown).

Note that while Group 3 showed a significant reduction compared to control, that Group did not show as much reduction as Groups 1 and 4. However, Group 3 still exhibited serviceable immunity, with a vaccine that is safer to the host than are the live vaccines of Groups 1 and 4.

Example 8

It was demonstrated that the transfer of purified populations of T-lymphocytes recovered from each of the above Groups 1, 3, and 4 conferred significant levels of protection to recipient naive mice challenged with *B. abortus* strain 2308 (data not shown).

In mice, antibodies and T-cells work together to limit challenge infections with strain 2308. By contrast, neither mice immunized with live RB51 nor mice immunized with irradiated RB51 produce antibodies that aid in eliminating the challenge strain. The immunity conferred by both types of RB51 vaccines appear to be wholly due to cell-mediated immunity. The usefulness of antibodies in eliminating brucellosis (other than in mice) is thought to be limited.

These data demonstrated that significant protection against challenge infection was achieved with gamma-irradiated *B. abortus* strain RB51. Further, the study demonstrated that cell-mediated immune responses to the gamma-irradiated vaccine were effective in conferring protection.

Example 9

The non-viable Brucella vaccine described above will be used to immunize cattle against Brucellosis.

Example 10

Because the gamma-irradiated Brucella vaccine will not cause infection, it is expected that this vaccine can be used in humans, which would make this the first effective Brucella vaccine suitable for use in humans. The active portion of the vaccine will be the irradiated Brucella strain described above, and this active portion will be administered in a pharmaceutically acceptable carrier.

Examples 11–13

Brucella vaccines otherwise as described above will be made, except that bleomycin, etoposide, or teniposide will be used as the mutagen in lieu of the gamma irradiation. These vaccines will be used to immunize mice, cattle, and humans against Brucella as otherwise described above.

Examples 14–42

Following the teachings of this specification, and making such appropriate modifications in the culturing and vaccination techniques described above as will occur to those of ordinary skill in the art who are given those teachings, vaccines will be made against the following facultative intracellular pathogens: *Brucella melitensis, Mycobacterium lepraemurum, Mycobacterium tuberculosis, Salmonella typhimurium*, Listeria, *Shigella flexneri, Rickettsia tsutsugamushi, Rickettsia prowazekii, Rickettsia rickettsii, Chlamydia psittaci, Chlamydia trachomatis, Chlamydia pneumoniae, Coxiella burnettii, Yersinia pestis, Legionella pneumonophia*, Francisella, *Blastomyces dermatitides, Histoplasma capsulatum*, Coccidioides, *Cryptococcus neoformans, Leishmania donovani, Leishmania mexicani, Trypanosoma cruzi, Toxoplasma gondi*, Plasmodium, Babesia, Theileria, Isospora, and Eimeria. These vaccines will be used to vaccinate suitable hosts against the corresponding virulent pathogens.

The entire disclosures of all references cited in this specification are hereby incorporated by reference. Also incorporated by reference is the entire disclosure of U.S. patent application Ser. No. 08/148,158, filed Nov. 5, 1993.

We claim:

1. A method for immunizing a mammalian host against infection by Brucella, comprising administering to the mammalian host a protective amount of a Brucella strain that has been subjected to an amount of ionizing radiation that is sufficient to make the strain non-viable.

2. A method as recited in claim 1, wherein the Brucella strain is administered to the mammalian host in conjunction with a pharmaceutically acceptable carrier.

3. A method as recited in claim 1, wherein said irradiated strain comprises *Brucella abortus.*

4. A method as recited in claim 3, wherein the Brucella strain is administered to the mammalian host in conjunction with a pharmaceutically acceptable carrier.

5. A method as recited in claim 1, wherein said irradiated strain comprises *Brucella melitensis.*

6. A method as recited in claim 5, wherein the Brucella strain is administered to the mammalian host in conjunction with a pharmaceutically acceptable carrier.

* * * * *